United States Patent [19]

Thompson et al.

[11] 4,301,684

[45] Nov. 24, 1981

[54] ULTRASONIC NON-DESTRUCTIVE EVALUATION TECHNIQUE FOR STRUCTURES OF COMPLEX GEOMETRY

[75] Inventors: Robert B. Thompson, Thousand Oaks, Calif.; Carmine F. Vasile, Huntington, N.Y.; Roger B. Houston, Newbury Park, Calif.

[73] Assignee: Rockwell International Corporation, El Segundo, Calif.

[21] Appl. No.: 117,157

[22] Filed: Jan. 31, 1980

[51] Int. Cl.³ ............................................. G01N 29/04
[52] U.S. Cl. ........................................ 73/602; 73/643
[58] Field of Search ................ 73/602, 643, 579, 609, 73/610

[56] References Cited

U.S. PATENT DOCUMENTS

| | | | |
|---|---|---|---|
| 4,052,889 | 10/1977 | Mucciardi et al. | 73/602 |
| 4,127,035 | 11/1978 | Vasile | 73/643 |
| 4,184,374 | 1/1980 | Thompson et al. | 73/643 |

*Primary Examiner*—Stephen A. Kreitman
*Attorney, Agent, or Firm*—H. Frederick Hamann; Craig O. Malin; John J. Deinken

[57] ABSTRACT

Disclosed is a method for evaluating the structural integrity of an object, including the steps of generating a lowest order horizontal shear wave in the object, detecting the wave after it has propagated through the object, time gating the detected signal to reject nonuseful portions, Fourier transforming the time response of the detected signal into a frequency dependent response, and predicting the structural integrity of the object from the characteristics of the frequency response.

9 Claims, 11 Drawing Figures

ULTRASONIC NON-DESTRUCTIVE EVALUATION TECHNIQUE FOR STRUCTURES OF COMPLEX GEOMETRY

GOVERNMENT RIGHTS

This invention was made in the course of or under a contract with the U.S. Air Force.

BACKGROUND OF THE INVENTION

This invention relates to signal processing techniques and, more particularly, to techniques for processing signals which are developed in ultrasonic nondestructive testing systems.

In recent years, nondestructive evaluation techniques have become increasingly important as a means for ascertaining the structural integrity of many different parts and assemblies. One particular branch within the field of nondestructive evaluation involves the use of ultrasonic waves. In the ultrasonic evaluation technique, ultrasonic energy is generated in an object to be tested and the ultrasonic waves which propagate in the object are analyzed, changes in the waves being attributable to the presence and character of flaws or other details of the structure in the object.

Although the use of these ultrasonic techniques has shown great promise, the technique has up to now been somewhat limited in application and has not heretofore been adaptable, for example, to analyze especially difficult evaluation tasks. These shortcomings may be exemplified by way of one particular evaluation problem involving the structural analysis of the wing of the United States Air Force C5A cargo aircraft. This wing incorporates a lapped joint which is connected by a row of fasteners secured through holes provided in the upper and lower halves of the joint. In order to ensure that a particular aircraft is in flyable condition, it is necessary to periodically inspect the area of the joint around these fastener holes to determine whether any cracks of a critical size have developed. Fatigue cracks which form at the fastener holes in the upper half of the joint may be detected by conventional nondestructive evaluation techniques, but the prior art has provided no nondestructive evaluation method, ultrasonic or otherwise, capable of determining whether a repairable fatigue crack has begun to grow from a fastener hole in the lower, inaccessible half of the joint.

Difficulties in evaluating the lower half of the C5A joint have arisen because of the complex geometry of the associated wing structure, which requires the acoustic wave to travel around corners to reach the region of interest, and because the joint includes a layer of sealant whose acoustic properties are substantially different from those of the air frame structure. As a result of these limitations, it has not been possible to effectively inspect the joint without disassembling the wing of the aircraft.

Consequently, as the above example indicates, a need has developed in the art for an ultrasonic testing technique capable of evaluating the structural integrity of objects shaped into complex geometries.

SUMMARY OF THE INVENTION

It is a general object of this invention to provide an improved technique for evaluating the structural integrity of an object.

A method of evaluating the structural integrity of an object, according to the present invention, includes the steps of:

(a) generating an acoustic signal in the object,
(b) detecting the acoustic signal after it has propagated in the object,
(c) transforming the response in time of the detected signal into a frequency dependent response, and
(d) predicting the structural integrity of the object from the characteristics of the frequency response.

In a preferred embodiment of the invention, a horizontally polarized shear wave is generated by a short pulse signal such that all modes higher than the lowest order mode are suppressed.

In more particular embodiments of the invention, step (b) may include either detecting that portion of the acoustic signal propagating in a direction approximately perpendicular to the direction in which the acoustic signal was generated or detecting that portion of the acoustic signal which was propagating in approximately the same direction as the generated acoustic signal.

In a preferred embodiment, step (c) further includes performing a Fourier transform of the detected signal to obtain a frequency dependent response.

An apparatus for evaluating the structural integrity of an object, according to the present invention, includes a transmitting transducer for generating an acoustic signal in the object, a receiving transducer for detecting the acoustic signal after it has propagated in the object, and a correlation processor for transforming the response in time of the detected signal into a frequency dependent response, the structural integrity of the object being related to the characteristics of the frequency response. The apparatus may further include a signal generator for driving the transmitting transducer.

These examples of the more important features of the invention are broadly outlined here in order to facilitate an understanding of the detailed description which follows, and so that the contributions which this invention provides to the art may be better appreciated. There are, of course, additional features of the invention which will be further described below and which are included within the subject matter of the appended claims.

BRIEF DESCRIPTION OF THE DRAWINGS

Additional objects, features, and advantages of the present invention will become apparent by referring to the following detailed description of the preferred embodiments in conjunction with the accompanying drawings, wherein the same reference numerals are used to refer to like elements throughout all the figures. In the drawings.

DESCRIPTION OF THE PREFERRED EMBODIMENT

Figure 1:
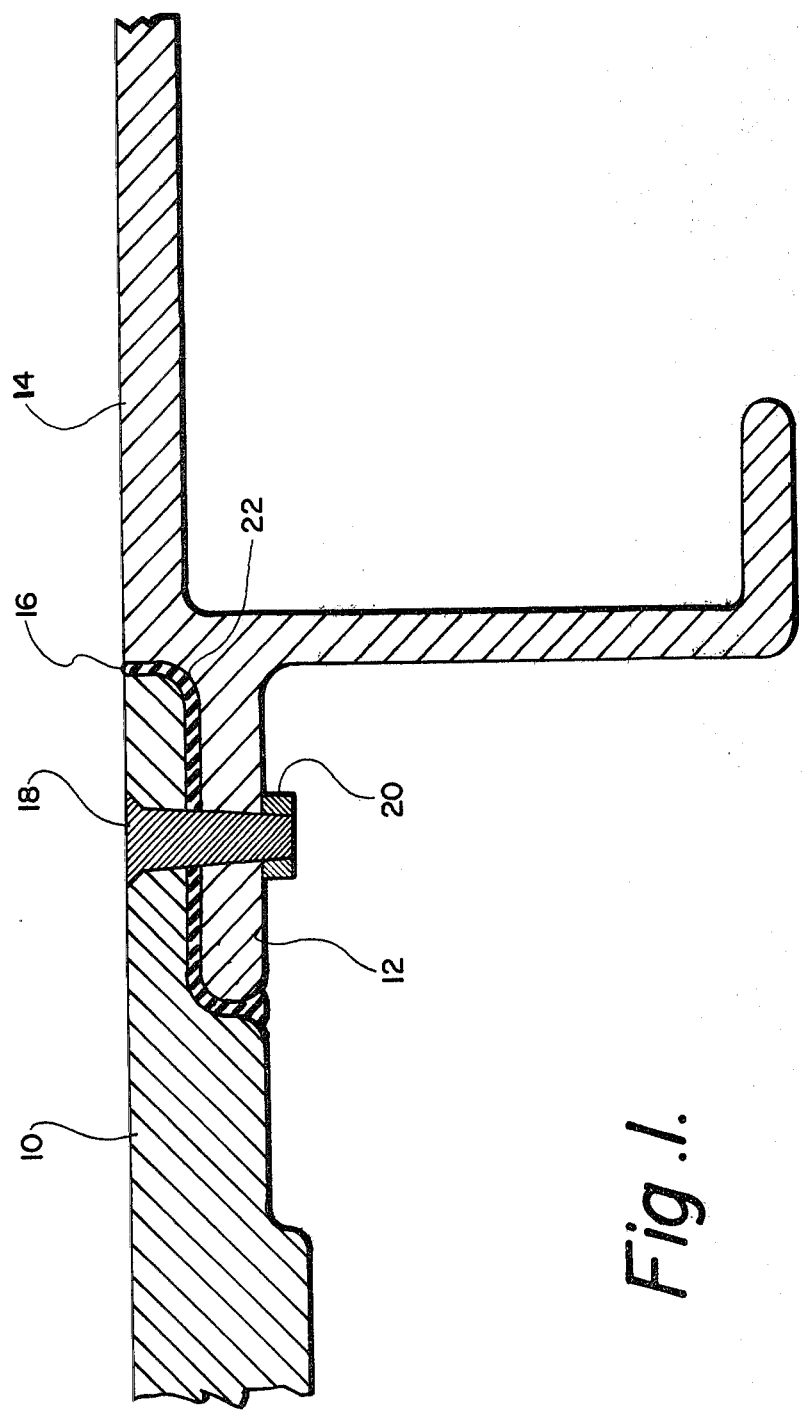
FIG. 1 is a cross-sectional representation of an aircraft wing joint.

Although those skilled in the art will appreciate the broader applications of the present invention, the invention may best be described with reference to the particular problem for which this technique was developed, which, as discussed briefly above, involved a lapped joint in the wing of the United States Air Force C5A cargo aircraft. A cross-sectional representation of that joint is shown in FIG. 1. The joint includes a first wing member 10, which overlaps a lip 12 projecting from a second wing member 14 to form the joint. A thin layer of sealant 16 is applied in the joint, with the members being secured by a number of tapered fasteners such as the fastener 18, which is attached with a nut 20 through corresponding holes in the first and second wing members.

A structural defect, such as a crack, is readily detectable, when it is present in the first member 10, by the use of conventional ultrasonic nondestructive testing methods. Flaw detection for defects in the lip region 12 of the second member, however, has proven to be considerably more difficult. A crack growing from a fastener hole in the lip cannot be directly detected because the lower half of the joint is inaccessible on an assembled aircraft. Additional complications are introduced by the attenuating properties of the sealant 16, the tapered shape of the fastener 18 and its associated attachment holes, and the complex geometry of the airplane structure, which includes the structural features shown in FIG. 1, as well as irregular fastener hole spacing, tapered wing member thickness, and a variable overlap dimension of the joint. The present invention provides a significant advance in the art and overcomes these restrictions by generating ultrasonic waves in the exposed portion of the second member 14, the wave energy from which then propagates around a corner 22 in the member 14 to reach the area of the fastener hole in the lip 12.

Figure 2:
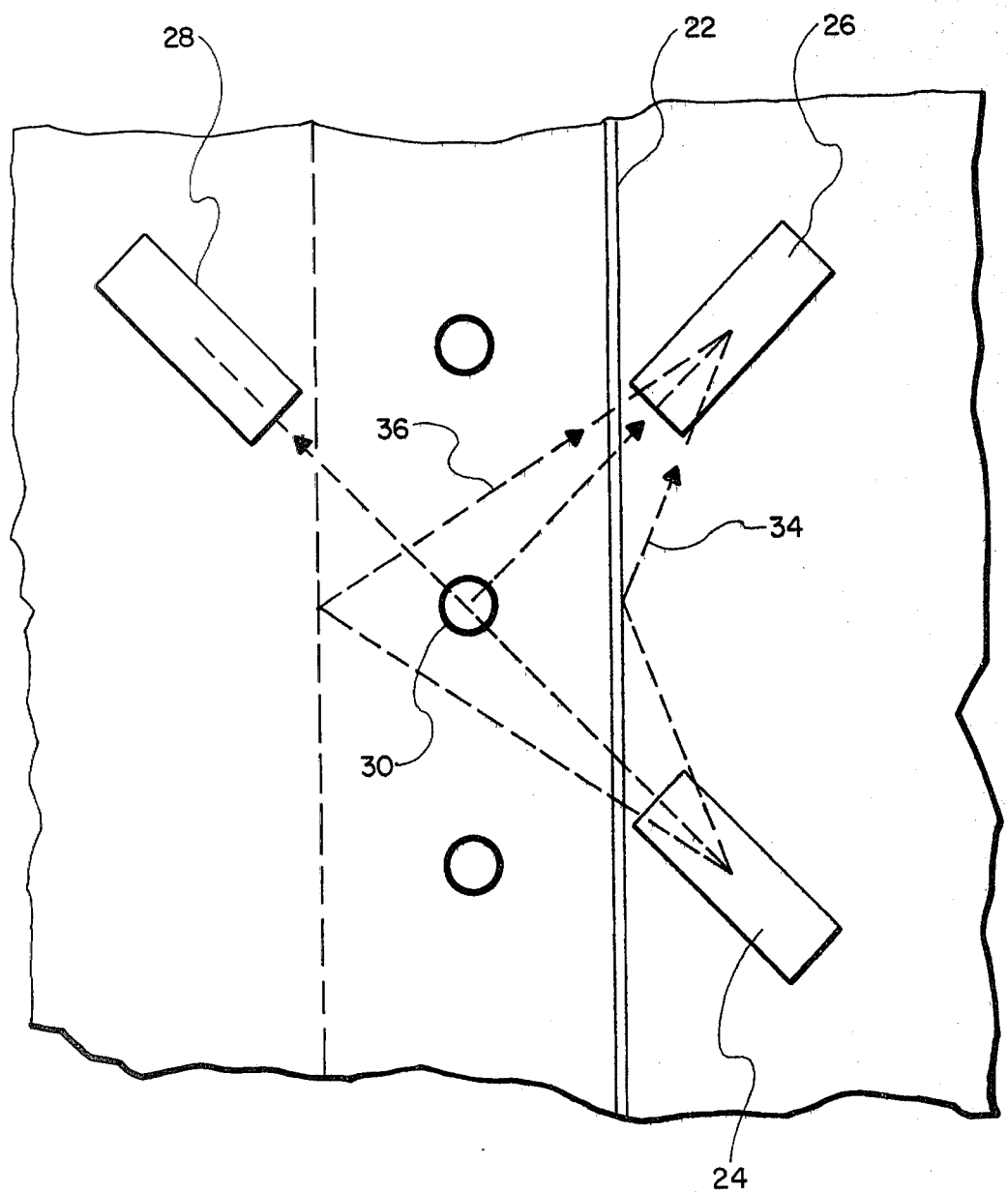
FIG. 2 is a top view of the joint shown in FIG. 1, illustrating transducer placement on the joint.

FIG. 2 is a top view of the joint shown in FIG. 1, illustrating one of a number of alternative positions for a transmitting transducer 24, and two receiving transducers 26 and 28, as they may be employed in the present invention. Those transducers which have been most advantageously used on the wing joint are electromagnetic acoustic transducers (EMATs), which are capable of generating and detecting ultrasonic waves in an electrically conductive object without contacting the object. The structure and operation of such transducers are discussed in further detail in U.S. Pat. Nos. 3,850,028; 4,104,922; and 4,127,035; the teachings of which are incorporated herein by reference. Periodic permanent magnet EMATs were utilized on the wing section to generate horizontally polarized shear (SH) waves, which were polarized parallel to the surfaces of the wing members. The SH type of wave is particularly useful for flaw detection in an object of complex geometry, such as the wing section illustrated, since a horizontal shear wave does not mode convert upon reflection from parallel surfaces and thus is capable of efficiently propagating around the corner 22 and on to the region of the fastener hole 30.

In the configuration illustrated in FIG. 2, the receiving transducer 26 was positioned to detect ultrasonic energy reflected at approximately 90° from the direction of travel of the wave generated by the transducer 24, while the second receiving transducer 28 was positioned to detect that portion of the wave travelling approximately straight through the fastener hole region.

The receiving transducer 28 is placed so that the properties of the fundamental $n=0$ SH wave mode which is transmitted through the wing joint can be utilized in the inspection scheme. By selecting the frequency of the $n=0$ mode, the low acoustic impedance of the sealant layer becomes negligible and the SH wave can thus propagate efficiently across the joint.

Although the characteristics of either the transmitted wave, as detected by the transducer 28, or the reflected wave, as detected by the transducer 26, can be utilized in characterizing the structural integrity of the region around the fastener hole 30, the detailed description herein will concentrate on an analysis of the reflected wave, although those skilled in the art will appreciate that an analogous procedure may be followed to employ the transmitted wave in a flaw detection scheme.

With the reflected signal transducer arrangement, a narrow section of the wing joint could be focused upon, since the back radiation patterns of the transducers 24 and 26 were not directed towards each other, even in the presence of a back reflecting edge. Although a higher frequency beam operating in a higher mode would seem desirable to achieve a better collimated beam and thereby reduce the effects of adjacent holes in the scattered field, a number of disadvantages have been found to accompany the operation of the present invention at higher frequencies. The operation frequency and excitation efficiency are strongly dependent on the thickness of the object at higher frequencies. Furthermore, bends, jogs, and other features of complex geometry in the object can affect higher order modes in a number of different ways. Finally, at higher frequencies, the structure may act as a waveguide, causing the ultrasonic energy to propagate extensively through the object and scatter from many features outside the particular area of interest.

Because of these problems associated with higher frequency operation, a set of transducers was selected to operate in the fundamental ($n=0$) horizontal shear mode, thereby rendering the operating frequency independent of the wing member thickness and minimizing the effects of transducer liftoff and the thickness of the wing member on the transducer excitation efficiency. The transducers were also located as closely as possible to the hole under inspection, as shown in FIG. 2, to obtain scattering measurements in the near field. The transmitter pulse used to drive the transmitting transducer was then limited in duration to a 2-5 cycle tone burst and the received signal was gated to reject the direct feedthrough signal as well as signals scattered from adjacent holes and other reflecting portions of the wing structure. With this arrangement, the area around the particular fastener hole being examined could be treated as an acoustic bandpass filter having a predictable phase and amplitude response. By taking this approach, the inspection scheme becomes one of displaying the complex Fourier transform of the received, time-gated signal, which is the product of the frequency response of a linear system composed of the wing structure, the transducers, and the associated electronics. The presence of a crack may then be expected to modify the passband shape of the structure and thereby produce a change in the Fourier transform.

Figure 3:
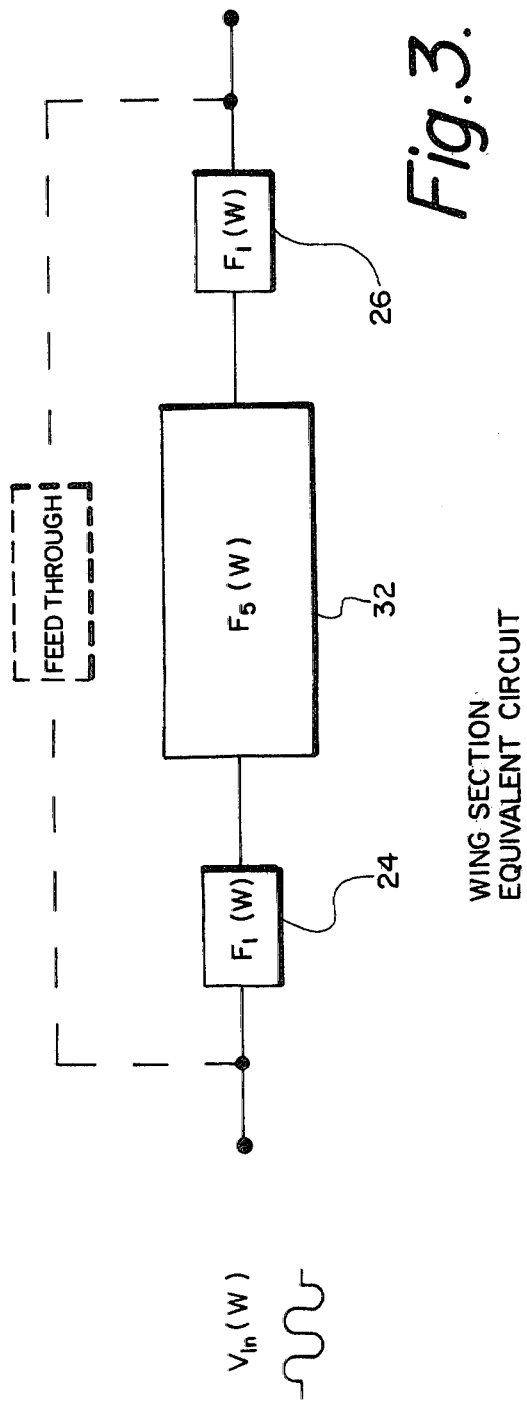
FIG. 3 is a block diagram schematic representing the propagation of an ultrasonic signal through the wing joint of FIG. 1.
Figure 4:
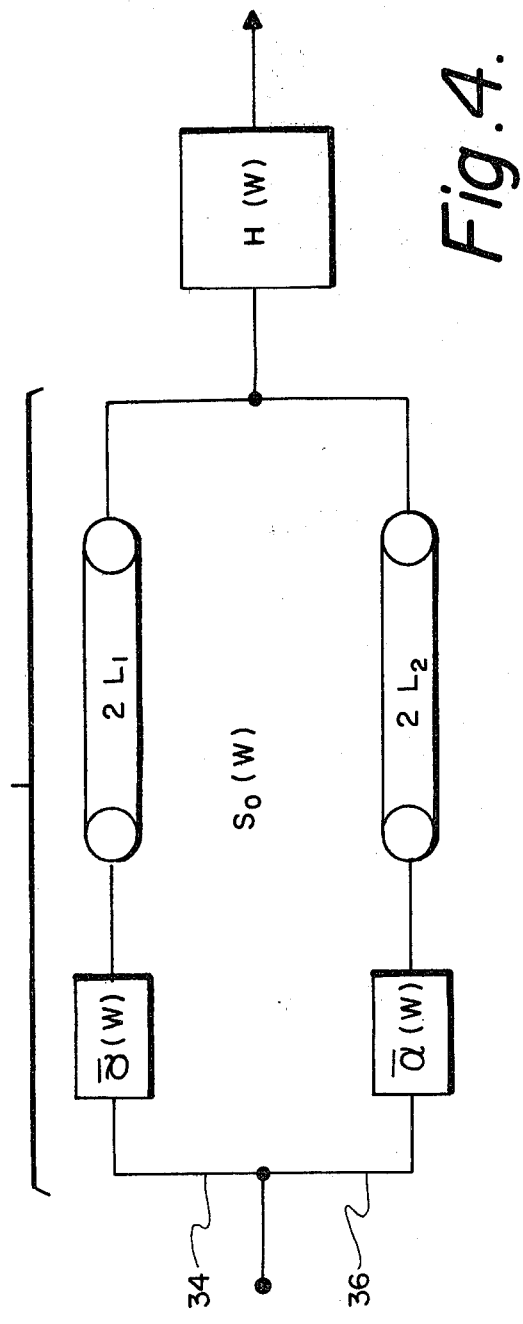
FIG. 4 is a schematic diagram which illustrates an equivalent circuit for the signal propagation model shown in FIG. 3.

FIG. 3 illustrates, in block diagram form, a schematic representation of the signal propagation process, treating the wing section as an acoustic filter. A tone burst $V_{in}(\omega)$ is applied to the transmitting EMAT 24, which has a filtering response $F_1(\omega)$, thereby exciting an n=0, SH wave. The SH wave is filtered by the wing section 32, with a filtering response $F_s(\omega)$, and subsequently is detected by a receiving EMAT 26, again with a filtering response $F_1(\omega)$, amplified, and filtered. The objective, under this approach, is to measure the effect of a crack on the wing section transfer function $F_s(\omega)$ and thereby deduce the length of the crack. To obtain this objective, the simplified equivalent circuit of FIG. 4 is derived as follows. $H(\omega)$ denotes an equivalent system impulse response which is determined by a calculation or by measuring the direct transmission of an SH wave between two transducers on a large plate of the same thickness as the wing section. In addition to the response of the EMATs, $F_1(\omega)$, the spectral characteristics of the driving voltage, $V_{in}(\omega)$, and of the receiving amplifier, $R(\omega)$, are included in $H(\omega)$ such that:

$$H(\omega) = V_{in}(\omega) \times F_1^2(\omega) \times R(\omega) \quad (1)$$

The actual wing section transfer function $F_s(\omega)$ is extremely difficult to calculate, since it depends upon a very complicated and analytically intractable structure. If, however, the frequency band of interest is restricted by an appropriate selection of $H(\omega)$, a first order approximation may be obtained by replacing $F_s(\omega)$ with $S_o(\omega)$, as shown in FIG. 4. This approximation depends on the assumption that energy can propagate from the transmitting EMAT 24 to the receiving EMAT 26 by either of the two paths 34 and 36 shown in FIG. 2. The first path 34 involves a reflection off the corner 22 of the second wing member 14, and is characterized by an amplitude transfer function $\bar{\gamma}(\omega)$ and a delay path $2L_1$. The second path 36, with a length $2L_2$ and an amplitude response $\bar{\alpha}(\omega)$, corresponds to energy entering the lip 12 and reflecting from the joint. $\bar{\alpha}(\omega)$ is the desired quantity since it will be affected by the presence and shape of the fastener hole. A third delay path corresponding to the hole location is not necessary, since little energy is scattered at 90° from a hole in a plate.

In order to develop a model, $H(\omega)$ and $S_o(\omega)$ can be calculated independently. Suitable expressions for SH wave excitation in a metal plate are developed in Vasile and Thompson, Periodic Magnet Noncontact Electromagnetic Acoustic Wave Transducer—Theory and Application, 1977 IEEE Ultrasonics Symposium Proceedings, Institute of Electrical and Electronic Engineers, Catalog No. CH1264-1SU, page 84, the teachings of which are incorporated herein by reference. The results presented in that paper can be simplified by assuming a zero skin depth, neglecting transducer end effects and diffraction, and noting that the forward transfer impedance is proportional to $\omega/\beta_n$, where $\beta_n$ is the SH plate mode propagation constant. With these assumptions, the frequency dependence of $H(\omega)$ is:

$$H(\omega) = H_o R(\omega) T(\omega)[Z_o(\omega) + Z_1(\omega) + \ldots ] \quad (2)$$

where $H_o$ is an arbitrary scale factor, $R(\omega)$ is the electronic receiver frequency response, and $T(\omega)$ is the Fourier transform of the input current waveform given approximately by $$T(\omega) \approx \sin c[\pi(f-f_o)N_c/f_o] \quad (3)$$

where $\omega = 2\pi f$, sin c x = (Sin x)/x, $N_c$ = number of carrier cycles, and $f_o$ = carrier frequency.

The bracketed portion represents the transducer response denoted $F_1^2(\omega)$.

The bracketed terms can be expressed as a sum of normalized forward transfer impedances of the plate modes which are dependent upon the EMAT parameters, plate material, and thickness. The first two modes are:

$$Z_o(\omega) \approx (\pi/2)^2 \operatorname{Sinc}^2\left[\frac{\pi(f-f_o)N}{f_o}\right] \quad (4)$$

$$\times \operatorname{sinc}^2\left[\frac{\pi}{2} \frac{f}{f_o}\right] e^{-i2\pi f/V_s L_D}$$

$$Z_1(\omega) \approx (\pi/2)^2 \frac{2}{\left[1 - \left(\frac{f_{cl}}{f}\right)^2\right]^{\frac{1}{2}}} \quad (5)$$

$$\times \operatorname{sinc}^2\left[\frac{\pi N}{f_o}\left(\sqrt{f^2 - f_{cl}^2} - f_o\right)\right]$$

$$\times \operatorname{Sinc}\left(\frac{\pi}{2} \frac{f}{f_o}\right) \sqrt{1 - \left(\frac{f_{cl}}{f}\right)^2} e^{-i2\pi f/V_s L_D} \sqrt{1 - \left(\frac{f_{cl}}{f}\right)^2}$$

$V_s$ is the shear wave velocity, $L_D$ is the length of the transmission path, $F_o$ is the shear wave velocity divided by the transducer period, $F_{cl}$ is the cutoff frequency for the n=1 mode, T is the thickness of the plate, and N is the number of periods in the transducers. Similar terms would be obtained for $Z_n(\omega)$, n>1. Experimental observations have shown that it is reasonable to neglect the n=1 mode in developing a first order model of the wing structure for the n=0 mode.

Turning now to the wing transfer function, $S_o(\omega)$ can be computed such that, when it is multiplied by the appropriate transfer function $H(\omega)$, the overall transfer function $S_o(\omega) H(\omega)$ which is measured is obtained. The result is $$S_o(\omega) = \bar{\gamma}(\omega)e^{-i2\omega L_1/V_s} + \bar{\alpha}(\omega)e^{-i2\omega L_2/V_s} \quad (6)$$

or $$S_o(\omega) = \bar{\gamma}(\omega)e^{-i2\omega L_1/V_s}\left[1 + \frac{\bar{\alpha}(\omega)}{\bar{\gamma}(\omega)}e^{-i2\omega(L_2-L_1)/V_s}\right] \quad (7)$$

Actual measurements suggest that $\bar{\gamma}(\omega)$ and $\bar{\alpha}(\omega)$ are slowly varying functions of frequency. Thus, it is useful to examine the behavior of Equation 7 with $\bar{\alpha}(\omega)/\bar{\gamma}(\omega)$ equal to a constant A:

$$|S_o(\omega)/2\bar{\gamma}(\omega)| = \begin{cases} \cos(\pi f \Delta \tau) & A = 1 \quad (8) \\ 1.25 + \cos(2\pi f \Delta \tau) & A = .5 \quad (9) \end{cases}$$

Consequently, a characteristic null in the Fourier transform of the system impulse response would be expected to correspond to destructive cancellation of the SH signals traveling along the two delay paths 34 and 36. If an obstruction, such as a crack emanating from the fastener hole, was introduced into the $L_2$ path, the null should be strongly affected. These predictions are, in fact, borne out by actual experimental results which have been obtained.

Figure 5:
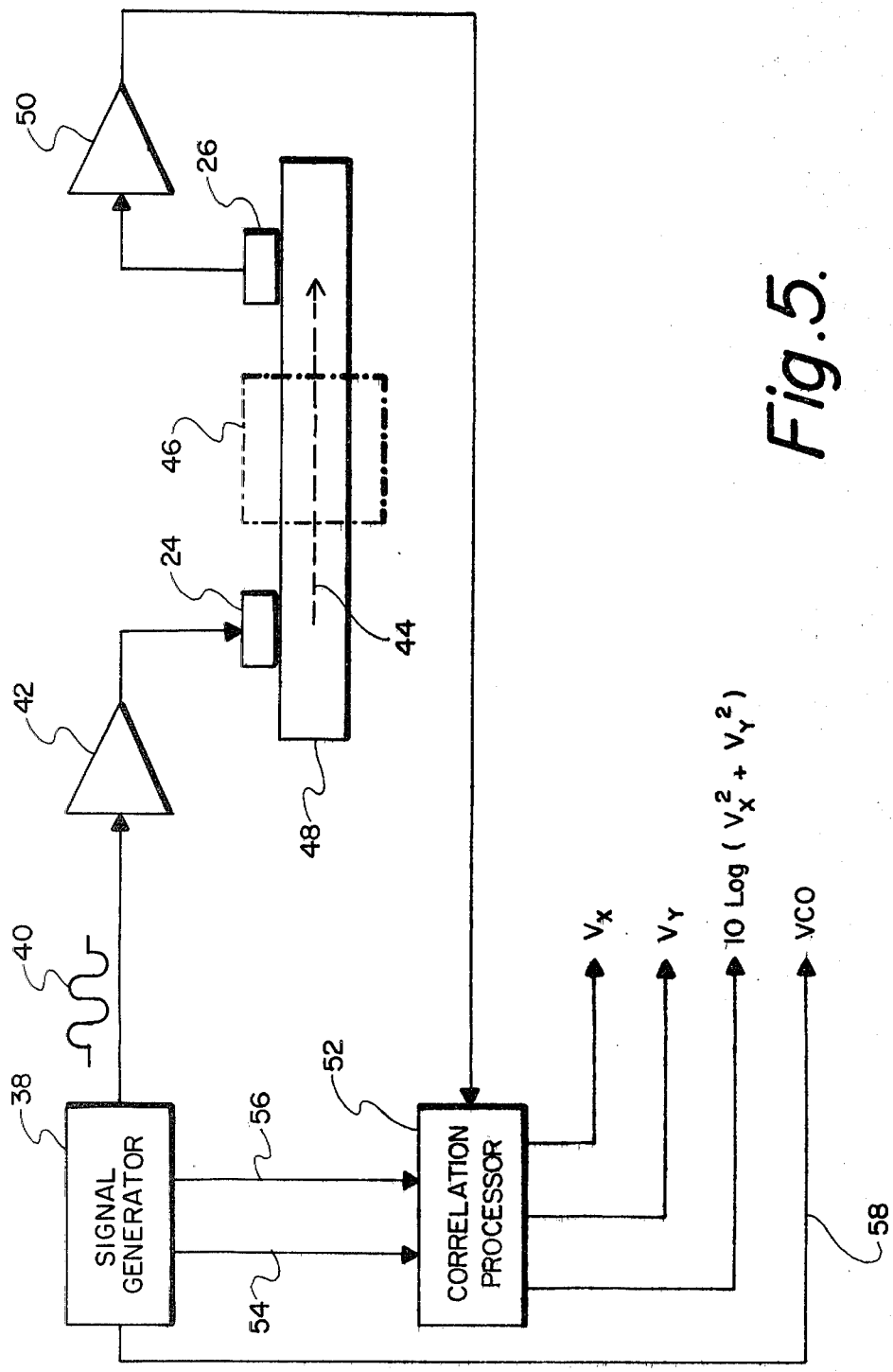
FIG. 5 is a schematic diagram illustrating an ultrasonic apparatus which is constructed according to the present invention for evaluating the structural integrity of a wing joint such as that shown in FIG. 1.

FIG. 5 illustrates the apparatus which was used to detect cracks in the C5A wing section. A signal generator 38 provides a short pulse signal 40 at a preselected frequency which is boosted by an amplifier 42 and applied to a transmitting transducer 24. The transducer 24 generates an ultrasonic signal 44 which propagates through a region 46 of the wing 48, the region 46 acting as an acoustic filter. The filtered signal is detected by a receiving transducer 26, boosted by an amplifier 50, and applied to a correlation processor 52, which also receives first and second reference signals 54 and 56 which are produced by the signal generator 38. The correlation processor provides voltage outputs representing $V_x$, $V_y$, and 10 log $(V_x^2 + V_y^2)$, as explained below in further detail in connection with FIG. 6.

Figure 6:
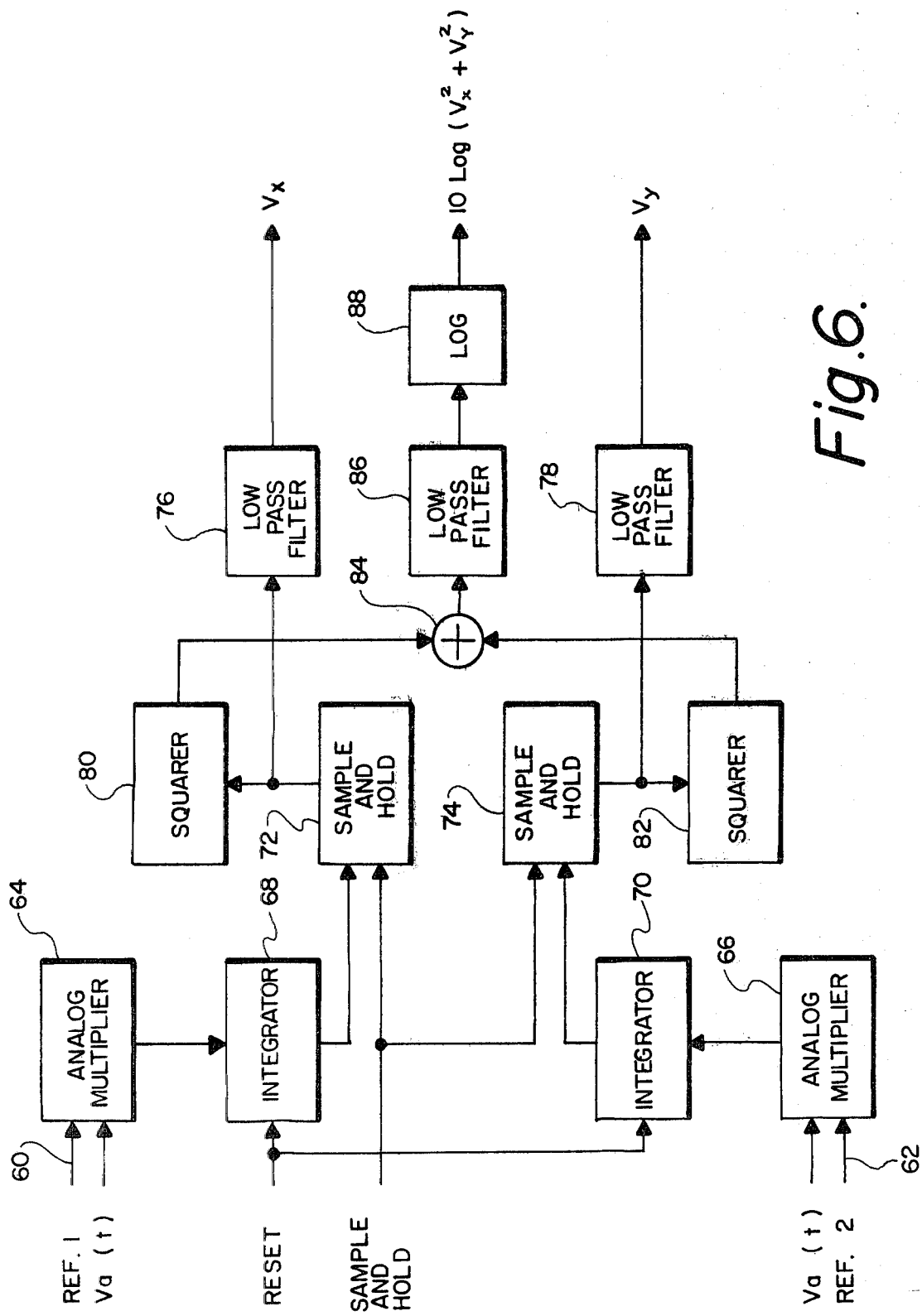
FIG. 6 is a block diagram schematic showing the correlation processor of FIG. 5 in more detail.

FIG. 6 is a schematic diagram in block form illustrating the correlation processor 52 of FIG. 5. The analog correlation processor forms the linear product of the received acoustic signals with a known, gated reference signal in order to derive both phase and amplitude information from the received signals. By using a voltage controlled oscillator (VCO) output 58 from the signal generator 38, it is possible to sweep the frequency of the gated reference and thus produce a real time plot corresponding to a Fourier transform of a time gated segment of the received acoustic signal. In FIG. 6, the Reference 1 and Reference 2 inputs 60 and 62 are identical TTL signals which are quarter cycle delayed with respect to each other and time delayed with respect to the main transmit TTL pulse burst. The reference signals are buffered and bandpass filtered in order to suppress higher harmonics which degrade the signal-to-noise ratio. The acoustic signal is combined with the reference signals in analog multipliers 64 and 66, the resulting products are integrated in integrators 68 and 70, and the integrands applied to sample and hold circuits 72 and 74. The sample and hold outputs are filtered in low pass filters 76 and 78, resulting in voltage outputs $V_x$ and $V_y$. The sample and hold outputs are also squared in the squarers 80 and 82 and summed together in an adder 84. The sum is filtered in a low pass filter 86 and the logarithm of the filtered output is computed by a log calculator 88, the output being 10 log $(V_x^2 + V_y^2)$.

The ideal output of the correlation processor may be approximated by:

$$V_x(\omega_R) = C \left( \int_{T_1}^{T_2} V_a(t) \cos\omega_R t \, dt \right) \quad (10)$$

$$V_y(\omega_R) = C \left( \int_{T_1}^{T_2} V_a(t) \sin\omega_R t \, dt \right)$$

where C is the constant of proportionality, controlled by the receiver gain adjust, and the brackets indicate that the average value over time is taken. If $V_a(t)$ is a signal which vanishes outside the range $T_1 < t < T_2$, then $V_x$ and $V_y$ are the real and imaginary parts of the Fourier transform $F(V_a)$, evaluated at $\Omega = \Omega_r$. Since the complex Fourier transform presents a smoother curve than the corresponding time wave form $V_a(t)$ in the case of overlapping time signals, it is a much simpler display to interpret.

Figure 7:
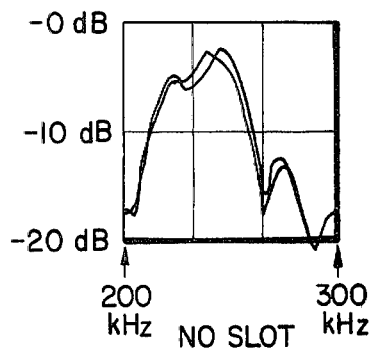
FIGS. 7-11 are frequency spectra plots displaying the results of the method of the present invention as it was performed on particular fastener holes in a wing joint mockup, for different conditions of structural integrity.
Figure 8:
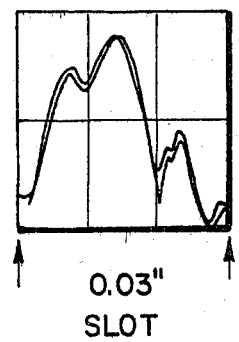
Figure 9:
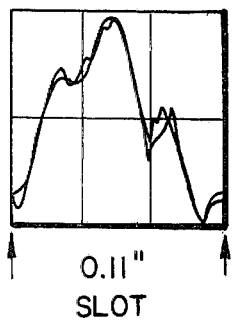
Figure 10:
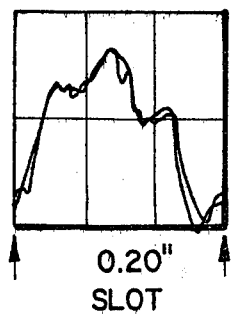
Figure 11:
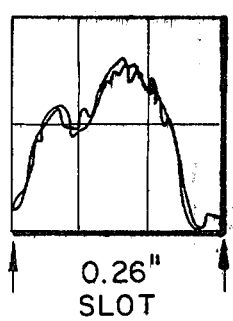

FIGS. 7–11 illustrate some results which were obtained using the technique of the present invention on a mockup of the C5A wing section as illustrated in FIG. 1. These figures are frequency spectrum plots obtained for fastener holes with different structural conditions imposed. FIG. 7 indicates the waveform obtained for a good hole with no flaws. FIGS. 8–11 represent the frequency spectra obtained for holes in which were placed slots of 0.03, 0.11, 0.20, and 0.26 inches, respectively. The slots were cut toward the outer edge of the lower lip 12 with a jeweler's saw. While the corresponding time dependent waveforms for these measurements would be very difficult to interpret, the power spectra in FIGS. 7–11 provide definite indications as to the condition of the various fastener holes. The sharp dip appearing in the power spectrum for an unslotted hole at 270 KHz, as in FIG. 7, is in good agreement with the simple model presented above. The frequency of the dip is at the predicted location and, as the slot length is increased, the amplitude of the dip is decreased, indicating that the depth of the dip at 270 KHz varies monotonically with slot length.

In conclusion, although typical embodiments of the present invention have been illustrated and discussed above, numerous modifications and alternative embodiments of the apparatus and method of this invention will be apparent to those skilled in the art in view of this description. Although the invention was described in terms of its application to the testing of a particular joint in an airplane wing, for example, it will be appreciated that the technique of the invention is applicable to a great variety of other testing situations. Accordingly, this description is to be considered as illustrative only and is provided for the purpose of teaching those skilled in the art the manner of constructing the apparatus and performing the method of this invention. Furthermore, it should be understood that the forms of the invention depicted and described herein are to be considered as the presently preferred embodiments. Various changes may be made in the configurations, sizes, and arrangements of the components of the invention, as will be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit obtained after reading the above description of the invention.

What is claimed is:

1. A method of evaluating the structural integrity of an object, comprising the steps of:
   (a) generating an acoustic signal in the object;
   (b) detecting the acoustic signal after it has propagated in the object;
   (c) transforming the response in time of the detected signal into a frequency dependent response;
   (d) comparing the passband of the frequency response, treating the object as an acoustic bandpass filter, to the passband for a standard object of known structural integrity; and
   (e) predicting the structural integrity of the object from the modified passband of the object.

2. The method of claim 1, wherein a short pulse is used to generate the acoustic signal and thereby include a band of frequencies within the signal.

3. The method of claim 1, wherein the generated acoustic signal comprises horizontally polarized shear waves.

4. The method of claim 3, wherein the acoustic signal is generated at a frequency such that all modes higher than the lowest order horizontal shear wave mode are suppressed.

5. The method of claim 1, wherein step (b) further comprises time gating the detected signal to reject nonuseful portions of the signal.

6. The method of claim 5, wherein step (b) further comprises detecting that portion of the acoustic signal propagating in a direction approximately perpendicular to the direction in which the acoustic signal was generated.

7. The method of claim 5, wherein step (b) further comprises detecting that portion of the acoustic signal propagating in approximately the same direction in which the acoustic signal was generated.

8. The method of claim 1, wherein step (c) further comprises performing a Fourier transform of the detected signal to obtain the frequency dependent response.

9. A method of evaluating the structural integrity of an object, comprising the steps of:
  (a) generating a lowest order horizontal shear wave in the object;
  (b) detecting the wave after it has propagated through the object;
  (c) time gating the detected signal to reject nonuseful portions;
  (d) Fourier transforming the time response of the detected signal into a frequency dependent response;
  (e) comparing the passband of the frequency response, treating the object as an acoustic bandpass filter, to the passband for a standard object of known structural integrity; and
  (f) predicting the structural integrity of the object from the modified passband of the object.

* * * * *